United States Patent
Benchikh et al.

(10) Patent No.: US 9,587,035 B2
(45) Date of Patent: Mar. 7, 2017

(54) ASSAY FOR BENZYLPIPERAZINE AND METABOLITES

(71) Applicant: Randox Laboratories Limited, Antrim (GB)

(72) Inventors: Elouard Benchikh, Antrim (GB); Ivan McConnell, Antrim (GB); Philip Lowry, Antrim (GB); Peter Fitzgerald, Antrim (GB)

(73) Assignee: Randox Laboratories Limited, Antrim (GB)

( * ) Notice: Subject to any disclaimer, the term of this patent is extended or adjusted under 35 U.S.C. 154(b) by 416 days.

(21) Appl. No.: 13/932,087

(22) Filed: Jul. 1, 2013

(65) Prior Publication Data

US 2014/0004623 A1  Jan. 2, 2014

(30) Foreign Application Priority Data

Jun. 29, 2012  (GB) .................... 1211634.9

(51) Int. Cl.
*C07K 16/44* (2006.01)
*C07D 295/096* (2006.01)

(52) U.S. Cl.
CPC .......... *C07K 16/44* (2013.01); *C07D 295/096* (2013.01); *C07K 2317/33* (2013.01); *C07K 2317/76* (2013.01); *C07K 2317/90* (2013.01)

(58) Field of Classification Search
CPC  C07K 16/44; C07K 2317/90; C07K 2317/76; C07K 2317/33; C07D 295/096
See application file for complete search history.

(56) References Cited

U.S. PATENT DOCUMENTS

| 7,632,929 B2* | 12/2009 | Owens .................... A61K 31/13 436/111 |
| 8,476,029 B2* | 7/2013 | Benchikh ........... G01N 33/9466 435/7.1 |
| 2013/0224882 A1* | 8/2013 | Benchikh ........... C07D 295/096 436/501 |

FOREIGN PATENT DOCUMENTS

| GB | EP 2261259 A1 * | 12/2010 | ............. C07K 16/44 |
| GB | WO 2010142974 A1 * | 12/2010 | ......... G01N 33/9466 |

OTHER PUBLICATIONS

Tuomola et al. Production and characterisation of monoclonal antibodies against a very samll hapten, 3-methylindole. J. Immunol. Methods 2000, vol. 240, pp. 111-124.*

Anita, U., et al., Validation of an LC-MS Method for the Detection and Quantification of BZP and TFMPP and their Hydroxylated Metabolites in Human Plasma and its Application to the Pharmacokinetic Study of TFMPP in Humans, J. Forensic Sci., Sep. 2010, vol. 55, No. 5, pp. 1311-1318.

Anita, U., et al., Pharmacokinetics of "party pill" drug N-benzylpiperazine (BZP) in healthy human participants, Forensic Science International, Mar. 3, 2009, vol. 186, pp. 63-67.

Fitzgerald, F., et al., Development of a High-Throughput Automated Analyzer Using Biochip Array Technology, Clinical Chemistry, May 12, 2005, vol. 51, No. 7, pp. 1165-1176.

(Continued)

*Primary Examiner* — Shafiqul Haq
(74) *Attorney, Agent, or Firm* — Hodgson Russ LLP

(57) ABSTRACT

The invention relates to the detection and quantification of 1-benzylpiperazine and its metabolites. The invention is underpinned by novel polyclonal antibodies with unique binding properties which enable immunoassay methods and kits for various applications.

3 Claims, 4 Drawing Sheets

(56) References Cited

OTHER PUBLICATIONS

Figure 1:
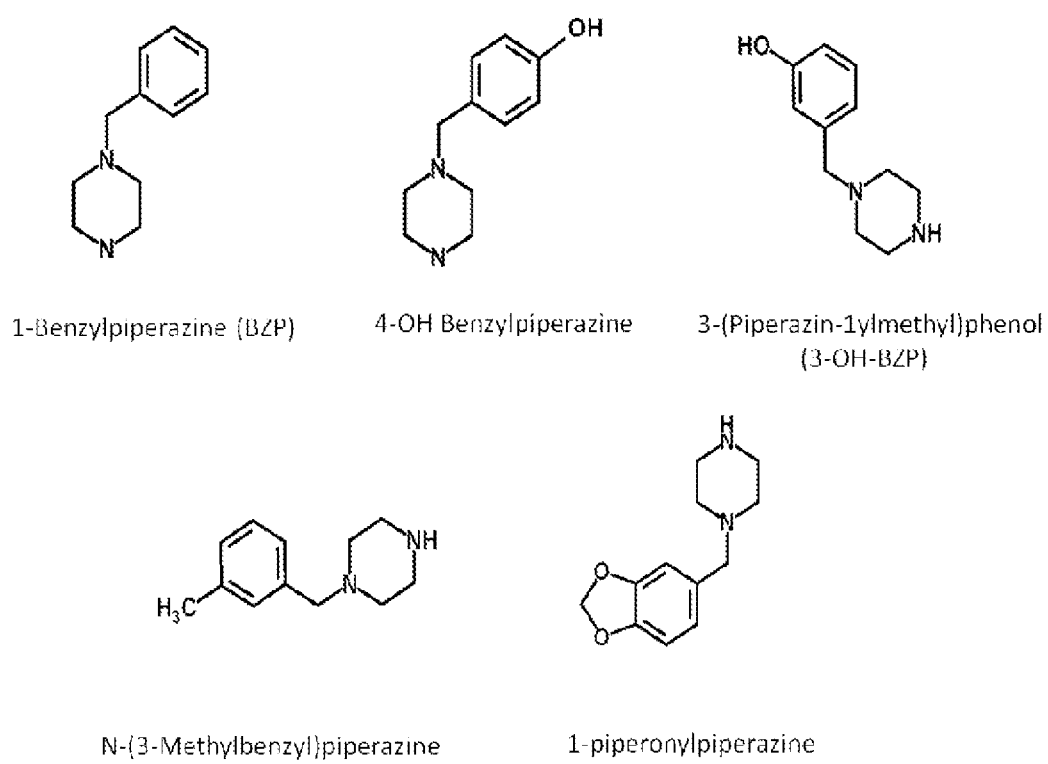

Logan, B., et al., Trazodone, meta-Chlorophenylpiperazine (an Hallucinogenic Drug and Trazodone Metabolite), and the Hallucinogenic Trifluoromethylphenylpiperazine Cross-React with the EMIT(R)II Ecstasy Immunoassay in Urine, JOurnal of Analytical Toxicology, Nov./Dec. 2010, vol. 34, pp. 587-589.

Peters, F. et al., Analytical Toxicology of Emerging Drugs of Abuse, Ther Drug Monit, Oct. 2010, vol. 32, No. 5, pp. 532-539.

Staack, R., et al., Piperazine-Derived Designer Drug 1-(3-Chlorophenyl)piperazine (mCPP): GC-MS Studies on its Metabolism and its Toxicological Detection in Rat Urine Including Analytical Differentiation from its Precursor Drugs Trazodone and Nefazodone, Journal of Analytical Toxicology, Nov./Dec. 2003, vol. 27, pp. 560-568.

Tsutsumi, H., et al., Metabolism and the Urinary Excretion Profile of the Recently Scheduled Designer Drug N-Benzylpiperazine (BZP) in the Rat, Journal of Analytical Toxicology, Jan./Feb. 2006, vol. 30, pp. 38-43.

\* cited by examiner

ASSAY FOR BENZYLPIPERAZINE AND METABOLITES

BACKGROUND

In recent years piperazine derivatives have emerged as a new class of designer drugs, gaining popularity especially among young people in the dance music scene, where they are commonly known as 'party pills'. They are often marketed as 'natural' or 'herbal' products, but are in fact entirely synthetic chemicals. Coupled with their ease of availability and varying legal status across the globe, this can create the misconception that these drugs are safe and without the risks commonly associated with traditional street drugs. Piperazine derivatives are usually found in illicit dosage forms as either tablets or capsules, but loose powders and, more rarely, solutions also occur. The tablets often carry logos similar to those seen on ecstasy tablets and they are often misleadingly sold as ecstasy or as apparent 'safer' and 'legal' alternatives.

Their name derives from the piperazine heterocycle, which is a common feature, and they can be divided into two sub-classes; the benzylpiperazines such as 1-benzylpiperazine (BZP) itself, and the phenylpiperazines, which include 1-(3-chlorophenyl)piperazine (mCPP), 1-(4-methoxyphenyl)piperazine (MeOPP), and 1-(3-Trifluoromethylphenyl)piperazine (TFMPP). Synonyms for BZP include 1-(phenylmethyl)piperazine, 1-Benzyl-1,4-diazacyclohexane, and N-benzylpiperazine. Street names include A2, Bliss, Charge, Frenzy, Herbal ecstasy, Legal E and Legal X.

1-Benzylpiperazine is metabolized in mammals by ring hydroxylation of the aromatic ring, N-dealkylation, O-methylation, and conjugation. Tsutsumi et al. (2006) suggested that p-hydroxy-BZP (p-OH-BZP) is the most relevant target analyte for use in forensic toxicological and clinical analysis of BZP intake, since it retains the structural identity of the parent molecule. Their study, conducted on Wistar rats, found that urinary levels of the parent BZP peaked at around 4 hrs post-dosing, while the levels of the OH-BZP metabolites, p-OH-BZP and m-hydroxy-BZP (m-OH-BZP)-(4-OH-BZP and 3-OH-BZP, respectively), reached maximum levels around 8hrs post-dosing. After the peak, they found that levels of BZP and its OH metabolites in urine dropped rapidly, with BZP becoming undetectable at 48hrs post dosing, while the p-OH-BZP and m-OH-BZP were detectable up to 48hrs post-dosing. Of the doses given in the study, 6.7% was excreted unchanged as the parent BZP molecule, 25% as p-OH-BZP (the most abundant primary metabolite), and 2% as m-OH-BZP. BZP can be detected in the plasma within 30 min of an oral dose of BZP hydrochloride, with peak plasma concentrations occurring between 60 min and 90 min post ingestion (Anita et al., 2009). BZP has an elimination half life of 5-6 hrs and elimination is complete by around 44 hrs.

Analytical methods which have been used to detect or determine piperazine derivatives include gas chromatography-mass spectrometry (GC-MS) and liquid chromatography-mass spectrometry (LC-MS) (Staack & Maurer, 2003; Antia et al., 2010). Peters et al. (2010) present a review of analytical toxicology of emerging drugs of abuse, including piperazines. A disadvantage of mass spectrometry based methods of detection is that they require expensive equipment and highly-trained staff.

Immunoassays are known in the art as relatively cost effective, simplistic, and rapid alternatives to mass-spectrometry-based analysis. A commercially available 3,4-methylenedioxy-N-methylamphetamine (MDMA) immunoassay, the EMIT® II Plus Ecstasy Assay (SYVA/Dade Behring), has been shown to have cross-reactivity to BZP, but concentrations of 3,000,000 ng/mL were needed for a positive result (Logan et al., 2010). Neogen Corporation (Lansing Mich., USA) have a specific benzylpiperazine ELISA kit available (Neogen Forensic Reference Brochure). However, no data are provided for the detection of metabolites such as the important 4-OH metabolite (p-OH-BZP) nor is it indicated that the kit has the ability to detect these metabolites. Therefore, there remains a need for a benzylpiperazine assay, which is not only sensitive to the parent molecule but that can also detect key metabolites to enable improvements in the forensic toxicological and clinical analysis of the intake of this designer drug.

REFERENCES

Antia, U. et al. (2009) *Forensic Sci Int,* 186(1-3):63-67.
Antia, U. et al. (2010) *J Forensic Sci,* 55(5):1311-1318.
Fitzgerald, S. P. et al. (2005). *Clin. Chem.,* 51: 1165-1176.
Logan, B. K. et al. (2010) *J Anal Toxicol,* 34:587-589.
Peters, F. T. et al. (2010) *Ther Drug Monit,* 32(5): 532-539.
Staack, R. F. & Maurer, H. H. (2003) *J Anal Toxicol,* 27(8):560-568.
Tsutsumi, H. et al. (2006) *J Anal Toxicol,* 30(1):38-43.
http://www.neogen.com/Toxicology/pdf/Forensic_Reference_Brochure.pdf

DRAWINGS

FIG. 1: Chemical Structures of BZP and Related Compounds
FIG. 2: Chemical Reactions of the Synthesis of Hapten-1
FIG. 3: Chemical Reaction of the Synthesis of Hapten-2
FIG. 4: Chemical Reactions of the Synthesis of Hapten-3

SUMMARY OF THE INVENTION

The present invention describes immunogens used in the production of novel polyclonal antibodies with unique binding properties, and which overcome the limitations of currently described immunoassays by enabling methods and kits for the detection and quantification of 1-Benzylpiperazine and its important metabolites 4-OH BZP and 3-OH BZP in in vitro patient samples. FIG. 1 shows the structures of these and other related molecules detected in the current invention.

According to a first aspect of the present invention, there is provided an immunogen having the general formula (0):

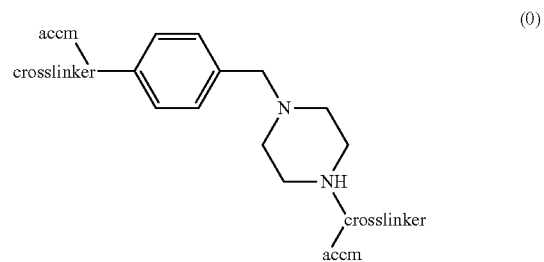

wherein accm is an antigenicity conferring carrier material; and crosslinker is a molecule attaching the accm to either the aromatic ring moiety or the piperazine moiety of the immunogen.

Optionally, the immunogen has the general structure (I):

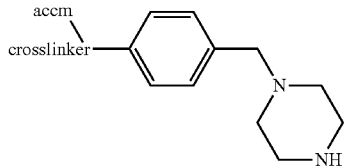

(I)

wherein accm is an antigenicity conferring carrier material; and crosslinker is a molecule attaching the accm to the aromatic ring moiety of the immunogen.

Optionally, the accm (antigenicity conferring carrier material) is selected from bovine serum albumin (BSA), egg ovalbumin, bovine gamma globulin, bovine thyroglobulin (BTG), keyhole limpet haemocyanin (KLH), synthetic poly(amino acids) having a sufficient number of available amino groups, lysine, and synthetic or natural polymeric materials bearing reactive functional groups. Further optionally, the accm is selected from bovine thyroglobulin (BTG) and bovine serum albumin (BSA). Still further optionally, the accm is bovine thyroglobulin (BTG). Alternatively, the accm is bovine serum albumin (BSA).

Optionally, the cross-linker has the general structure (II):

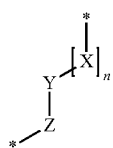

(II)

wherein
X, when present, is attached to the aromatic ring moiety of the immunogen and is selected from —C(O)—, O, and NH;
n=0 or 1;
Y is selected from a $C_1$-$C_{10}$, preferably a $C_1$-$C_6$, substituted or unsubstituted, straight or branched chain alkylene moiety; and a $C_1$-$C_{10}$, preferably a $C_1$-$C_6$, substituted or unsubstituted, straight or branched chain arylene moiety; and
Z (before conjugation with the accm) is selected from a carboxyl, a dithiopyridyl, a maleimidyl, an amino, a hydroxyl, a thiol, a thioester, and an aldehyde moiety.

Optionally, the immunogen has the general structure (I), wherein accm is bovine serum albumin (BSA); and the cross-linker has the general structure (II), wherein n=1; X is present and is attached to the aromatic ring moiety of the immunogen and is O; Y is a $C_1$ unsubstituted alkylene moiety; and Z (before conjugation with the accm) is a carboxyl moiety.

Optionally, the immunogen has the general structure (I), wherein accm is bovine thyroglobulin (BTG); and the cross-linker has the general structure (II), wherein n=1; X is present and is attached to the aromatic ring moiety of the immunogen and is O; Y is a $C_1$ unsubstituted alkylene moiety; and Z (before conjugation with the accm) is a carboxyl moiety.

Alternatively, the cross-linker has the general structure (II):

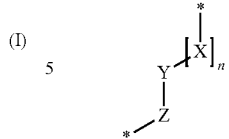

(II)

wherein
X, when present, is attached to the piperazine moiety of the immunogen and is selected from —C(O)—, O, and NH;
n=0 or 1;
Y is attached to the piperazine moiety of the immunogen and is selected from a $C_1$-$C_{10}$, preferably a $C_1$-$C_6$, substituted or unsubstituted, straight or branched chain alkylene moiety, and a $C_1$-$C_{10}$, preferably a $C_1$-$C_6$, substituted or unsubstituted, straight or branched chain arylene moiety; and
Z (before conjugation with the accm) is selected from a carboxyl, a dithiopyridyl, a maleimidyl, an amino, a hydroxyl, a thiol, a thioester, and an aldehyde moiety.

Optionally, the immunogen has the general structure (I), wherein accm is bovine serum albumin (BSA); and the cross-linker has the general structure (II), wherein n=0; Y is attached to the piperazine moiety of the immunogen and is a $C_2$ unsubstituted alkylene moiety; and Z (before conjugation with the accm) is a carboxyl moiety.

Optionally, the immunogen has the general structure (I), wherein accm is bovine thyroglobulin (BTG); and the cross-linker has the general structure (II), wherein n=0; Y is attached to the piperazine moiety of the immunogen and is a $C_2$ unsubstituted alkylene moiety; and Z (before conjugation with the accm) is a carboxyl moiety.

According to a second aspect of the present invention, there is provided an antibody derivable from an immunogen according to the present invention.

Optionally, the antibody is a polyclonal antibody. Alternatively, the antibody is a monoclonal antibody. Further alternatively, the antibody is an antibody fragment, optionally a single chain variable fragment.

Optionally, the antibody has an $IC_{50}$ selected from one or more of: about 1 ng/ml for 1-benzylpiperazine (BZP), about 1 ng/ml for 4-OH benzylpiperazine (4-OH-BZP; p-OH-BZP), about 1 ng/ml for 3-(Piperazin-1ylmethyl)phenol, about 1 ng/ml for 1-Piperonylpiperazine, and about 3 ng/ml for N-(3-Methylbenzyl)piperazine.

Further optionally, the antibody has an $IC_{50}$ selected from one or more of: at least 1.4 ng/ml for 1-benzylpiperazine (BZP), 0.813 ng/ml for 4-OH benzylpiperazine (4-OH-BZP; p-OH-BZP), 1.137 ng/ml for 3-(Piperazin-1ylmethyl)phenol, 1.379 ng/ml for 1-Piperonylpiperazine, and about 2.646 ng/ml for N-(3-Methylbenzyl)piperazine.

Optionally, the antibody is capable of binding to at least one epitope of an analyte selected from 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine.

According to a third aspect of the present invention, there is provided a method of preparing an antibody capable of binding to at least one epitope of an analyte selected from 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine; the method comprising raising the antibody against an immunogen according to the present invention.

Optionally, the raising step comprises preparing an antiserum. Further optionally, the raising step comprises preparing an antiserum by immunizing an animal. Still further optionally, the raising step comprises preparing an antiserum by immunizing an animal and isolating antibodies from the animal.

According to a fourth aspect of the present invention, there is provided an antibody derivable from the method according to the third aspect of the present invention.

Optionally, the antibody is a monoclonal antibody. Alternatively, the antibody is a polyclonal antibody. Further alternatively, the antibody is an antibody fragment, optionally a single chain variable fragment.

Optionally, the antibody has an $IC_{50}$ selected from one or more of: about 1 ng/ml for 1-benzylpiperazine (BZP), about 1 ng/ml for 4-OH benzylpiperazine (4-OH-BZP; p-OH-BZP), about 1 ng/ml for 3-(Piperazin-1ylmethyl)phenol, about 1 ng/ml for 1-Piperonylpiperazine, and about 3 ng/ml for N-(3-Methylbenzyl)piperazine.

Further optionally, the antibody has an $IC_{50}$ selected from one or more of: at least 1.4 ng/ml for 1-benzylpiperazine (BZP), at least 0.813 ng/ml for 4-OH benzylpiperazine (4-OH-BZP; p-OH-BZP), at least 1.137 ng/ml for 3-(Piperazin-1ylmethyl)phenol, at least 1.379 ng/ml for 1-Piperonylpiperazine, and of at least 2.646 ng/ml for N-(3-Methylbenzyl)piperazine.

Optionally, the antibody is capable of binding to at least one epitope of an analyte selected from 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine.

According to a fifth aspect of the present invention, there is provided a method of detecting or determining one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine; the method comprising contacting a sample with an antibody according to the present invention; detecting or determining the quantity of the antibody; and attributing the presence or amount of the antibody to the presence or amount of one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine in the sample.

Optionally, the method comprises the further step of detecting or determining the quantity of a label or detecting agent capable of binding to the antibody according to the present invention for detecting or determining the quantity of the antibody.

Also disclosed is an assay for detecting or determining one or more of 1-benzylpiperazine (BZP), 4-OH benzylpiperazine (4-OH-BZP; p-OH-BZP), 3-(Piperazin-1ylmethyl) phenol, 1-Piperonylpiperazine and N-(3-Methylbenzyl)piperazine; the assay comprising an antibody according to the present invention; and means for detecting or determining the quantity of the antibody in the sample.

Optionally, the assay further comprises a solid support to which the antibody is conjugated.

Also disclosed is a kit for detecting or determining one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine; the kit comprising an antibody according to the present invention.

Alternatively, the kit for detecting or determining one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine comprises a detecting agent according to the present invention and an antibody capable of binding one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine.

Optionally, the kit further comprises instruction for use.

According to a further aspect of the present invention, there is provided a method of detecting or determining one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine; the method comprising contacting a sample with an antibody capable of binding one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine; and a detecting agent; and attributing the presence or amount of the detecting agent to the presence or amount of one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine in the sample.

Optionally, the detecting agent has the general structure (I), wherein accm is horseradish peroxidase (HRP); and the cross-linker has the general structure (II), wherein n=1; X is present and is attached to the aromatic ring moiety of the immunogen and is O; Y is a $C_1$ unsubstituted alkylene moiety; and Z (before conjugation with the accm) is a carboxyl moiety.

Optionally, the detecting agent has the general structure (I), wherein accm is horseradish peroxidase (HRP); and the cross-linker has the general structure (II), wherein n=0; Y is attached to the piperazine moiety of the immunogen and is a $C_2$ unsubstituted alkylene moiety; and Z (before conjugation with the accm) is a carboxyl moiety.

DETAILED DESCRIPTION

Unless otherwise stated, technical terms as used herein are used according to the conventional usage as known to those skilled in the art.

The invention provides an immunogen of structure:

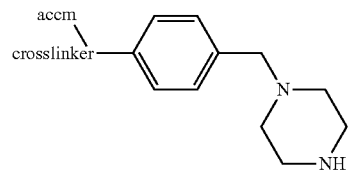

wherein accm is an antigenicity conferring carrier material; and in which the crosslinker optionally has the general structure:

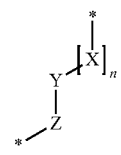

wherein,

X, when present, is attached to the aromatic ring moiety of the immunogen and is selected from —C(O)—, O, and NH;

n=0 or 1;

Y is a $C_1$-$C_{10}$, preferably a $C_1$-$C_6$, substituted or unsubstituted, straight or branched chain alkylene moiety, or a $C_1$-$C_{10}$, preferably a $C_1$-$C_6$, substituted or unsubstituted, straight or branched chain arylene moiety; and Z (before conjugation with the accm) is selected from a carboxyl, a dithiopyridyl, a maleimidyl, an amino, a hydroxyl, a thiol, a thioester, and an aldehyde moiety.

In the field of antibody development, it is generally considered that the optimum length of the crosslinker—the linking group joining the analyte to be detected to the accm (straight chain length and not including hydrogen atoms)—is about 1-10 atoms, more usually about 1-6 atoms.

Before conjugation to the accm, the molecule can be referred to as a hapten. The term "hapten" as used herein describes a pre-immunogenic molecule that stimulates antibody production only when conjugated to a larger carrier molecule (accm).

Once the hapten is conjugated to the accm, it forms the immunogen. The term "immunogen" as used herein describes an entity that induces an immune response such as production of antibodies or a T-cell response in a host animal. The accm can be any material that makes all or part of the hapten susceptible to antibody recognition and binding. For example, the accm can be a protein, a protein fragment, a synthetic polypeptide, or a semi-synthetic polypeptide. Illustrative examples of useful antigenicity-conferring carrier materials are bovine serum albumin (BSA), egg ovalbumin, bovine gamma globulin, bovine thyroglobulin (BTG), keyhole limpet haemocyanin (KLH), etc. Preferably the accm is BTG.

A further aspect of the invention relates to antibodies obtained or derived from immunogens according to the invention, and that bind to an epitope of one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine.

The term "antibody" as used herein refers to an immunoglobulin or immunoglobulin-like molecule. In a preferred embodiment of the current invention, the antibodies are polyclonal antibodies but the skilled person will understand that any type of immunoglobulin molecule or fragment thereof can be used, for example monoclonal antibodies, Fab fragments, scFv fragments and any other antigen binding fragments, all of which fall within the scope of the current invention. The polyclonal antibodies of the current invention may be produced by any method known to those skilled in the art. Any suitable host animal may be used, preferably a mammalian animal, for example but not limited to sheep, rabbit, mouse, guinea pig, and horse.

When used in reference to an antibody, the word 'specific' or 'specificity' in the context of the current invention refers to the analyte that is preferably bound by the antibody, as gauged by a suitable metric such as the cross-reactivity i.e. the analyte with the greatest cross-reactivity is the antibody-specific analyte and is generally given a value of 100%, with all other analytes accorded a value relative to this value of 100%. In addition, as is known by one skilled in the art, for cross-reactivity to be of practical use, the analyte-specific antibody must display a high sensitivity as measured by a suitable metric such as the $IC_{50}$. The $IC_{50}$ is a common measure of antibody sensitivity for immunoassays. For the current invention, a high sensitivity is an $IC_{50}$ of less than 50 ng/ml, preferably less than 10 ng/ml, most preferably around 1 ng/ml. In the current invention an $IC_{50}$ of around 1 ng/ml refers to antibodies with $IC_{50}$ values from about 0.5ng/ml and above. It is recognized that for immunoassays that utilize a competitive format, the exact $IC_{50}$ value varies slightly depending on the nature of the detecting agent used to compete with the analyte in the sample. The high sensitivity of the current antibodies to BZP and 4-OH BZP, as measured by $IC_{50}$, enables the use of the antibodies in toxicological applications.

A further aspect of the invention relates to antibodies that have an $IC_{50}$ of about 1 ng/ml for 1-benzylpiperazine (BZP), about 1 ng/ml for 4-OH benzylpiperazine (4-OH-BZP; p-OH-BZP), about 1 ng/ml for 3-(Piperazin-1ylmethyl)phenol, about 1 ng/ml for 1-Piperonylpiperazine, and about 3 ng/ml for N-(3-Methylbenzyl)piperazine.

A still further aspect of the invention relates to antibodies that have an $IC_{50}$ of at least 1.4 ng/ml for 1-benzylpiperazine (BZP), at least 0.813 ng/ml for 4-OH benzylpiperazine (4-OH-BZP; p-OH-BZP), at least 1.137 ng/ml for 3-(Piperazin-1ylmethyl)phenol, at least 1.379 ng/ml for 1-Piperonylpiperazine, and of at least 2.646 ng/ml for N-(3-Methylbenzyl)piperazine. It is known to the skilled person that, by varying the antibody concentration through dilution, the $IC_{50}$ values can be adjusted depending upon the application.

The invention also provides methods of detecting or determining one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine in an in vitro sample of an individual or an environmental sample; the method comprising contacting the sample with one or more detecting agents and one or more antibodies, optionally one or more antibodies of the invention; detecting or determining the quantity of the one or more detecting agents; and deducing from calibrators, the presence of or amount of one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine in the sample.

The antibody may be an antibody according to the present invention or may be any antibody capable of binding one or more of 1-benzylpiperazine (BZP), 4-OH benzylpiperazine (4-OH-BZP; p-OH-BZP), 3-(Piperazin-1ylmethyl)phenol, 1-Piperonylpiperazine, and N-(3-Methylbenzyl)piperazine.

'Detecting' as referred to herein means qualitatively analyzing for the presence or absence of a substance in a sample, while 'determining' means quantitatively analyzing for the amount of a substance in a sample. The detecting agent is a small molecule (generally of similar structure to a molecule to be detected) conjugated to a labelling/detecting agent that is able to bind to one of the antibodies of the invention. The labelling agent is selected from an enzyme, a luminescent substance, a radioactive substance, or a mixture thereof. Preferably, the labelling agent is an enzyme, preferably a peroxidase, most preferably horseradish peroxidase (HRP). Alternatively or additionally, the luminescent substance may be selected from a bioluminescent, chemiluminescent, and fluorescent material. For the purposes of the invention, the patient sample to be used for in vitro analysis can be hair or a peripheral biological fluid but is preferably selected from whole blood, serum, plasma, and urine.

A further aspect of the invention relates to a kit for detecting or determining one or more of 1-benzylpiperazine (BZP), 4-OH benzylpiperazine 94-OH-BZP; p-OH-BZP), 3-(Piperazin-1ylmethyl)phenol, 1-Piperonylpiperazine, and N-(3-Methylbenzyl)piperazine; the kit comprising one or more antibodies of the invention.

Alternatively or additionally, the kit comprises one or more detecting agents of the invention.

Optionally, the kit may contain one or more detecting agents and one or more calibrators.

General Methods, Examples and Results

Preparation of Haptens, Immunogens and Detecting Agents

Although haptens provide defined structural epitopes, they are not in themselves immunogenic and therefore need to be conjugated to carrier materials (accm), which will elicit an immunogenic response when administered to a host animal. Appropriate carrier materials (accm) commonly contain poly(amino acid) segments and include polypeptides, proteins and protein fragments. Illustrative examples of useful carrier materials are bovine serum albumin (BSA), egg ovalbumin, bovine gamma globulin, bovine thyroglobulin (BTG), keyhole limpet haemocyanin (KLH), etc.

Alternatively, synthetic poly(amino acids) having a sufficient number of available amino groups, such as lysine, may be employed, as may other synthetic or natural polymeric materials bearing reactive functional groups.

The coupling chemistry used to prepare an immunogen from a hapten and carrier protein is an important consideration for the successful production and the correct specificity of the resultant antibodies. The choice of cross-linking methodology is governed both by the functional groups present on the carrier protein and the hapten, and by the orientation of the hapten desired for appropriate presentation to the immune system.

Also, carbohydrates, yeasts, or polysaccharides may be conjugated to the hapten to produce an immunogen.

The haptens can also be coupled to a detectable labelling agent such as an enzyme (for example, horseradish peroxidase), a substance having fluorescent properties, or a radioactive label for the preparation of detecting agents (conjugates) for use in the immunoassays.

For example, carbodiimide-mediated coupling methods can be used to couple haptens to a detectable labelling agent. In such carbodiimide-mediated coupling methods, the carbodiimide, for example the water-soluble carbodiimide 1-ethyl-3-(3-dimethylaminopropyl)carbodiimide (EDC), first reacts with available carboxylic groups of the haptens to form a highly active O-acylisourea intermediate. The activated carboxylic group then reacts with the primary amine to form an amide bond, with the release of the carbodiimide, for example EDC, mediator as a soluble isourea derivative. The detectable labelling agent, for example fluorescent substance, may be a monovalent residue of fluorescein or a derivative thereof.

Immunogen formation for the invention described herein involves conventional conjugation chemistry as described in "Bioconjugation Techniques" by Greg T. Hermanson, Academic Press, pages 419-455 and "Bioconjugation" by Mohammed Aslam and Alastair Dent, ISBN 1-561 59-1 61-0 (1998) pages 364-482. In order to confirm that adequate conjugation of the hapten to carrier material has been achieved, prior to immunisation, each immunogen is evaluated using matrix-assisted UV laser desorption /ionisation time-of-flight mass spectroscopy (MALDI-TOF MS).

General Procedure for MALDI-TOF Analysis of Immunogens.

MALDI-TOF mass spectrometry was performed using a Voyager STR Biospectrometry Research Station laser-desorption mass spectrometer coupled with delayed extraction in accordance with the manufacturer's instruction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Preparation of Antisera

In order to generate polyclonal antisera, 2 mg of an immunogen according to the present invention was prepared in PBS, mixed at a ratio of 50% Immunogen in PBS with 50% Freund's Complete adjuvant (Sigma, Product Number—F5881) and emulsified by repeatedly passing the mixture through a tip on the end of a 1 ml syringe, until it reached the required semi-solid consistency. 1 ml of the mixture was then injected into a host animal, such as rabbit, sheep, mouse, guinea pig or horse. Sheep were the preferred host animal. Further injections (boosts) were administered on a monthly basis (1 mg of immunogen is prepared in PBS and mixed at a ratio of 50% Immunogen in PBS with 50% of Freunds Incomplete Adjuvent, Sigma product Number—F5506) until the required titre was achieved. Serum was sampled for evaluation of the antibody titre.Briefly, blood was collected by applying pressure to the exposed jugular vein and inserting a clean 14 gauge hypodermic needle to remove 500 ml of blood per sheep, under gravity. The blood was stored at 37° C. for a minimum of 1 hour before the clots were separated from the side of the centrifuge bottles using disposable 1 ml pipettes (ringing). The samples were stored at 4° C. overnight. Samples were then centrifuged at 4200 rpm for 30 minutes at 4° C. The serum was poured off and centrifuged again, at 10,000 rpm for 15 minutes at 4° C., before being aliquoted and stored at <−20° C. The Immunoglobulin (Ig) fraction was extracted from the antisera via caprylic acid/ammonium sulphate precipitation of immunoglobulin.

The antibody titre was evaluated by coating a microtitre plate (Thermo Fisher Scientific NUNC, 468667) with antibody (125 µl/well) in coating buffer (10 mM Tris pH 8.5) at 37° C. for 2 hours. The plate was then washed 4 times over 10 minutes with working strength TBST. 50 µl of sample/standard (1-Benzylpiperazine) was added to the appropriate wells in triplicate, followed by 75 µl of hapten-HRP conjugate and incubated at 25° C. for 1 hour. The plate was then washed and 125 µl of 3,3',5,5'-Tetramethylbenzidine (TMB) (Randox, 4380-15) added to each well and left at room temperature for 20 mins in the dark. The reaction was stopped using 125 µl of 0.2M sulphuric acid. The absorbances were read at 450nm with an ELISA microplate reader (BIO-TEK instruments, Elx800) and the means calculated. Antibody sensitivity was then be determined.

When the optimal titre had been attained, the host animal was bled to yield a suitable volume of specific antiserum (overall this resulted in 20 bleeds in total, with approximately 200 ml of antiserum achieved per bleed). The degree of antibody purification required depends on the intended application. For many purposes, there is no requirement for purification. However, in other cases, such as where the antibody is to be immobilised on a solid support, purification steps can be taken to remove undesired material and eliminate non-specific binding. Various purification steps are available if required, including Immunoglobulin Precipitation (as described above), Antigen-specific affinity purification, Size-exclusion chromatography and Ion Exchange Chromatography.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunizing an animal, preferably a mammalian animal, by repeated administration of an immunogen. The serum from the immunized animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal antibodies. This can be carried out using an ELISA based format as described above for measuring antibody titre or as a Biochip based format. Details of how the antibodies are fixed to the Biochip are described in FitzGerald, S. P. et al, Clin. Chem. 51(7); 1165-1176; 2005. The signal emitted in the immunoassay is proportionate to the amount of detecting agent bound to the antibodies which in turn is inversely proportionate to the analyte concentration. The signal can be detected or quantified by comparison with a calibrator.

Figure 2:
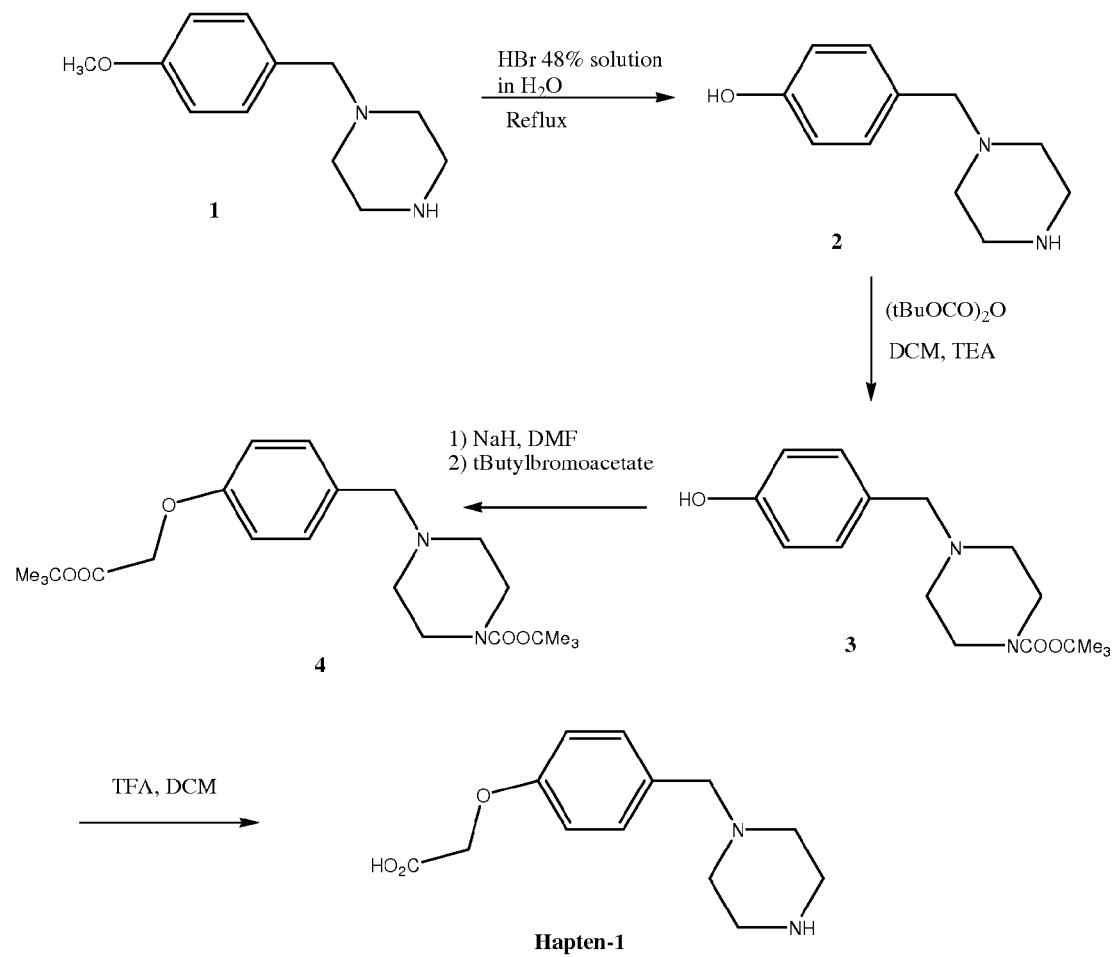
Figure 3:
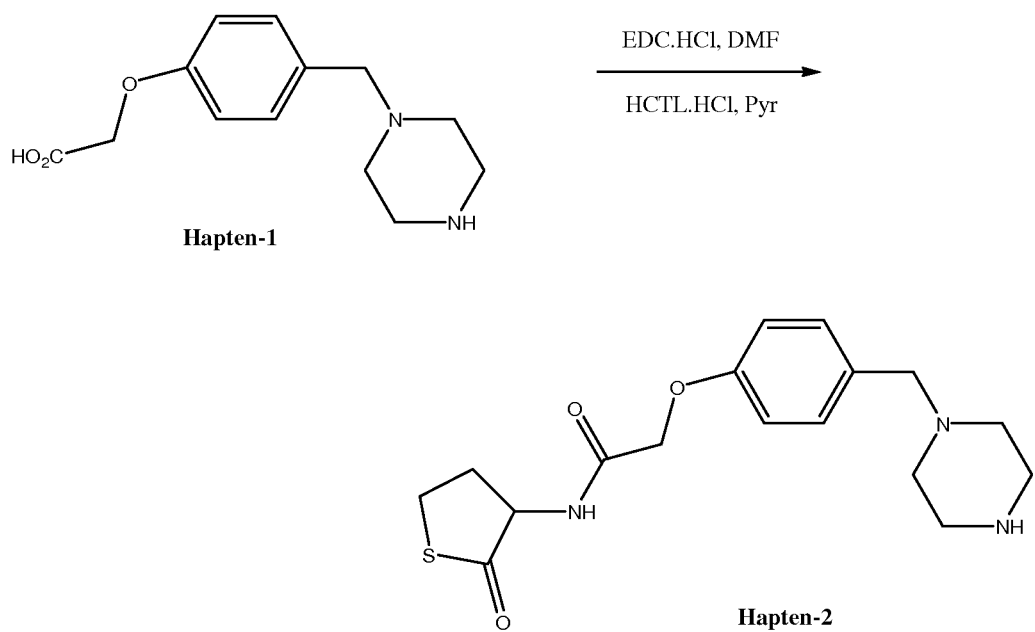
Figure 4:
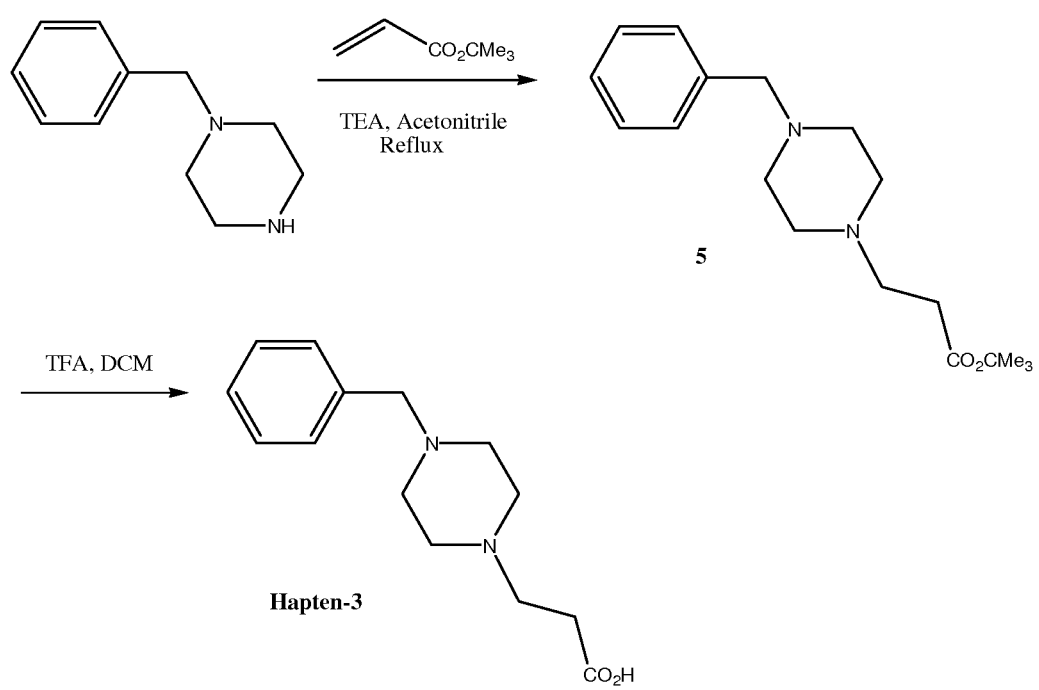

EXAMPLES (Numbers in bold refer to structures in FIG. 2 or FIG. 4)

Example 1

Preparation of 4-hydroxybenzylpiperazine dihydrobromide 2

To a solution of hydrobromic acid 48% in water (100 ml) was added 4-methoxybenzylpiperazine hydrochloride 1 (10 g, 41.2 mM) and the suspension was heated at reflux for 4 hours. The solution was then cooled to room temperature and concentrated to dryness to give a solid. Water was then added to the solid and the solution was stirred for 1 hour. The solid was then filtered, washed by water and dried at high vacuum to give the 4-hydroxybenzylpiperazine dihydrobromide 2 (6.3 g, 43.2%)

Example 2

Preparation of N-boc-4-hydroxybenzylpiperazine 3

To a suspension of 4-hydroxybenzylpiperazine dihydrobromide 2 (6 g, 18.9 mM) in dichloromethane (150 ml) was added TEA (3.15 ml, 22.7 mM) and BOC anhydride (4.9 g, 22.6 mM) and the mixture was stirred at room temperature overnight. The solution was then washed by water (1×100ml), brine (1×100 ml), dried over sodium sulphate, filtered and concentrated to dryness. The crude product obtained was purified by flash chromatography on silica gel using ethyl acetate/hexane (50/50) to give the N-boc-4-hydroxybenzylpiperazine 3 (4.1 g, 74.2%).

Example 3

Preparation of the Ester 4

To a suspension of sodium hydride (NaH) (0.551 g, 16.4 mm) in dimethylformamide (DMF) (50 ml) under nitrogen was added drop-wise a solution of N-boc-4-hydoxybenzylpiperazine 3 (4.0 g, 13.7 mM) in DMF (25 ml) and the mixture was stirred and heated at 60° C. for 1 hour. The mixture was then cooled to room temperature and to it was added drop-wise a solution of tert-butyl bromoacetate (3.2 g, 16.4 mM) in DMF (25 ml) and the mixture was stirred and heated at 60° C. for 4 hours. The solution was then cooled to room temperature (RT) and the DMF was removed under vacuum. Ethyl acetate (200 ml) was added to the crude product and then washed by water (100 ml) and brine. The solution was then dried over sodium sulphate, filtered and concentrated to dryness. The crude product obtained was purified by chromatography on silica gel using ethyl acetate/hexane (1/1) to give the ester 4 (4.0 g, 72%) as a clear oil.

Example 4

Preparation of the 2-[4-(piperazin-1-yl-methyl)phenoxy]acetic acid TFA salt (Hapten-1)

To a solution of the ester 4 (3.5 g, 8.6 mM) in dichloromethane (60 ml) was added trifluoroacetic acid (TFA) (30 ml) and the solution was stirred at RT overnight. The solution was concentrated to dryness and the crude product obtained was triturated with ether to give a white solid of the hapten-1 as TFA salt (2.7 g, 86%) as TFA salt. (As illustrated in FIG. 2)

Example 5

Conjugation of Hapten-1 to BSA (Immunogen-I)

To a solution of 2-[4-(piperazin-1-yl-methyl)phenoxy] acetic acid TFA salt (Hapten-1) (49.5 mg, 0.15 mM) in DMF (1.0 ml) was added N,N-dicyclohexylcarbodiimide (DCC) (33.08 mg, 0.16 mM) and N-hydroxysuccinimide (18.7 mg, 0.16 mM) and the mixture was stirred at room temperature overnight. The dicyclohexylurea formed was removed by filtration and the solution was added drop-wise to a solution of BSA (150 mg, 2.3 μmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried.MALDI results showed 11.95 molecules of hapten-1 had been conjugated to one molecule of BSA.

Example 6

Conjugation of Hapten-1 to BTG (Immunogen-II)

To a solution of 2-[4-(piperazin-1-yl-methyl)phenoxy] acetic acid TFA salt (Hapten-1) (61.99 mg, 0.203 mmol) in DMF (1.0 ml) was added N, N-dicyclohexylcarbodiimide (DCC) (46.01 mg, 0.223 mmol) and N-hydroxysuccinimide (25.66 mg, 0.223 mmol) and the mixture was stirred at room temperature overnight. The dicyclohexylurea formed was removed by filtration and the solution was added drop wise to a solution of BTG (150 mg, 2.25 μmol) in 50 mM sodium bicarbonate solution (pH 8.5) (10 ml).

The mixture was then stirred overnight at 4° C. The solution was then dialysed against 50 mM phosphate buffer pH 7.2 (3 changes) for 24 hours at 4° C., and freeze-dried.

Example 7

Conjugation of Hapten-1 to HRP

EDC hydrochloride (10 mg) was dissolved in water (0.5 ml) and immediately added to a solution of 2-[4-(piperazin-1-yl-methyl)phenoxy]acetic acid TFA salt (Hapten-1) (2 mg) in DMF (0.2 ml). After mixing, this solution was added drop wise to a solution of HRP (20 mg) in water (1 ml).

Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Example 8

Preparation of tert-butyl 4-(4-benzylpiperazin-1-yl) propionate

To a solution of 1-benzylpiperazine (8.813 g, 0.05 mol) in acetonitrile (200 ml) under nitrogen was added triethylamine (TEA) (16.7 ml, 0.12 mol) and tert-butyl acrylate (15.4 g, 0.12 mol) and the mixture was stirred at reflux overnight. The solution was then cooled to RT and concentrated to dryness. Ethyl acetate (300 ml) was then added and the ethyl acetate phase was washed by water (200 ml), brine (200 ml), dried over sodium sulfate, filtered and concentrated to dryness. The crude product obtained was purified by chromatography on silica gel using 70% ethyl acetate, 30% hexane to give the tert-butyl 4-(4-benzylpiperazin-1-yl) propionate 5 as an oil (12.6 g, 83%).

Example 9

Preparation of 4-(4-benzylpiperazin-1-yl) propionic acid TFA salt (Hapten-3)

To a solution tert-butyl 4-(4-benzylpiperazin-1-yl) propionate 5 (12.2 g, 0.04 mol) in dichloromethane (200 ml) was added trifluoroacetic acid (TFA) (50 ml) and the mixture was then stirred at RT for 6 hours. The mixture was concentrated to dryness and the crude product obtained was triturated with ether and the solid formed was filtered, washed with ether and dried under vacuum overnight to give 4-(4-benzylpiperazin-1yl) propionic acid TFA salt (Hapten-3) (10.5, 72%). (As illustrated in FIG. 4)

Example 10

Conjugation of Hapten-3 to BSA (Immunogen-III)

To a solution of 4-(4-benzylpiperazin-1-yl) propionic acid TFA salt (Hapten-3) (54.35 mg, 0.15 mM) in DMF (1.0 ml) was added N, N-dicyclohexylcarbodiimide (DCC) (33.08 mg, 0.16 mM) and N-hydroxysuccinimide (18.7 mg, 0.16 mM) and the mixture was stirred at room temperature overnight. The dicyclohexylurea formed was removed by filtration and the solution was added drop-wise to a solution of BSA (150 mg, 2.3 µmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried. MALDI results showed 6.03 molecules of hapten-3 had been conjugated to one molecule of BSA.

Example 11

Conjugation of Hapten-3 to BTG (Immunogen-IV)

To a solution of 4-(4-benzylpiperazin-1-yl) propionic acid TFA salt (Hapten-3) (73.55 mg, 0.203 mmol) in DMF (1.0 ml) was added N, N-dicyclohexylcarbodiimide (DCC) (46.01 mg, 0.223 mmol) and N-hydroxysuccinimide (25.66 mg, 0.223 mmol) and the mixture was stirred at room temperature overnight. The dicyclohexylurea formed was removed by filtration and the solution was added drop wise to a solution of BTG (150 mg, 2.25 µmol) in 50 mM sodium bicarbonate solution (pH 8.5) (10 ml).

The mixture was then stirred overnight at 4° C. The solution was then dialysed against 50 mM phosphate buffer pH 7.2 (3 changes) for 24 hours at 4° C., and freeze-dried.

Example 12

Conjugation of Hapten-3 to HRP

EDC hydrochloride (10 mg) was dissolved in water (0.5 ml) and immediately added to a solution of 4-(4-benzylpiperazin-1-yl) propionic acid TFA salt (Hapten-3) (2 mg) in DMF (0.2 ml). After mixing, this solution was added drop wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Example 13

Development of a Biochip Immunoassay

Pre-immunisation blood samples were collected from 16-month-old female Suffolk sheep. The immunisation mixture was prepared by adding 2 mg of immunogen prepared in PBS at a ratio of 50% lmmunogen/PBS with 50% Freund's Complete adjuvant (Sigma, Product Number—F5881) and emulsifying the mixture to prepare the final product for immunisation. On Day 0, each sheep was immunized intramuscularly with 1 ml of the mixture described above, with 2-[4-(piperazin-1-yl-methyl)phenoxy]acetic acid conjugated to a carrier protein bovine thyroglobulin (BTG) (as in example 6 above). Subsequent boosts (a total of 20 boosts) were administered intramuscularly to each sheep every 30 days. Freund's complete adjuvant (Sigma, Product Number—F5881) was used for primary immunizations and Freund's incomplete adjuvant (Sigma product Number—F5506) was used for all subsequent injections. Routine bleeds were taken between boosts to monitor the antibody titre and sensitivity, using hapten 1 conjugated to Horseradish peroxidase in a competitive ELISA, testing cross reactivity to 1-Benzylpiperazine and 4-OH benzylpiperazine.

Once the antibody titres were assessed as meeting the required performance criteria i.e. there was no significant increase in antibody titre and a plateau had been reached in the % displacement profile, antibodies were then evaluated by competitive immunoassay. They were first immobilized on a biochip platform (9 mm×9 mm) (Randox Laboratories Ltd.), which was the vessel for the immunoreactions. The semi-automated bench top analyser Evidence Investigator was used (EV3602, Randox Laboratories Ltd., Crumlin, UK, patents-EP98307706, EP98307732, EP0902394, EP1227311, EP1434995 and EP1354623). The assay principle was based on competition for binding sites of the polyclonal antibodies between free antigen (1-Benzylpiperazine and other cross-reactants) and labelled conjugate (Hapten 1-HRP, prepared as in example 6). Assay diluent (155 µl), calibrator/1-benzylpiperazine or potential cross-reactant (25 µl) followed by Hapten 1-HRP conjugate (120 µl) were added to the appropriate biochip. The biochips were then incubated for 30 minutes at 30° C. on a thermo-shaker set at 370 rpm. The biochips were then subjected to 2 quick wash cycles using the wash buffer provided, followed by 4×2 minute wash cycles. 250 μl of signal (1:1 luminol+ peroxide, v/v) was then added to each biochip, and after 2 minutes the biochip carrier was imaged in the Evidence Investigator analyser. The system incorporates dedicated software to automatically process, report and archive the data generated (details can be found in FitzGerald, S. P. et al, *Clin. Chem.* 51(7); 1165-1176; 2005).

Results

Calibration curves were generated using the Biochip based immunoassay as described above. The $IC_{50}$ was calculated from the graphs by taking 50% of the signal from the zero calibrator and reading the corresponding value on the x-axis, equivalent to the concentration of unlabelled ligand which reduces specific binding of labelled ligand by 50%. Specificity was also tested against a range of related analytes (Table 1). Cross-reactivity was calculated according to the following formula:

% CR=$IC_{50}$, 1-benzylpiperazine/$IC_{50, CR}$×100 where % CR is the percentage cross-reactivity, $IC_{50}$, 1-benzylpiperazine is the concentration of 1-benzylpiperazine that causes 50% displacement of signal and $IC_{50, CR}$ is the concentration of 1-benzylpiperazine/metabolites/structurally-related molecules that causes 50% displacement of signal.

TABLE 1

Antibody characterisation using antiserum raised to Immunogen II and detecting agent derived from Hapten-1 in a competitive assay format (CR based on 100% for 1-benzylpiperazine)

| Analyte | % Cross-reactivity | IC50 |
| --- | --- | --- |
| 1-Benzylpiperazine | 100.0 | 1.4 ng/ml |
| 4-OH Benzylpiperazine | 172.1 | 0.8 |
| 3-(Piperazin-1ylmethyl)phenol diHCl | 123.7 | 1.1 |
| 1-Piperonylpiperazine | 101.5 | 1.4 |
| N-(3-Methylbenzyl)piperazine diHCl | 52.9 | 2.6 |
| 1-(3-Methylphenyl)piperazine | 3.9 | 35.9 |
| 1-Phenylpiperazine | 3.4 | 41.2 |
| 1-(2-Methoxyphenyl)piperazine diHCl | 3.2 | 43.8 |
| 1-(3-Trifluoromethylphenyl)piperazine HCl | 1.9 | 73.7 |
| 1-(4-Methylphenyl)piperazine | 1.3 | 107.7 |

TABLE 1-continued

Antibody characterisation using antiserum raised to Immunogen II and detecting agent derived from Hapten-1 in a competitive assay format (CR based on 100% for 1-benzylpiperazine)

| Analyte | % Cross-reactivity | IC50 |
| --- | --- | --- |
| 1-(3-Hydroxyphenyl)piperazine | 1.0 | 140 |
| mCPP HCl | 0.6 | 233.3 |

The invention claimed is:

1. An antibody derived from an immunogen having the general structure (I):

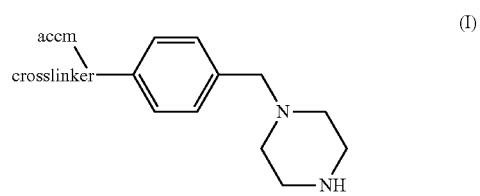

wherein accm is an antigenicity conferring carrier material; and crosslinker is a molecule attaching the accm to the aromatic ring moiety of the immunogen; and wherein the antibody specifically recognizes 1-benzylpiperazine and wherein the antibody has at least 100% cross-reactivity with 4-OH benzylpiperazine and has less than 1% cross reactivity with 1-(3-chlorophenyl) piperazine (mCPP) as compared to 100% cross-reactivity with said 1-benzylpiperazine.

2. The antibody of claim 1, wherein the antibody has an IC50 of: about 1 ng/ml for 1-benzylpiperazine (BZP), about 1 ng/ml for 4-OH benzylpiperazine (4-OH-BZP; p-OH-BZP), about 1 ng/ml for 3-(Piperazin-1ylmethyl)phenol, about 1 ng/ml for 1-Piperonylpiperazine, and about 3 ng/ml for N-(3-Methylbenzyl)piperazine.

3. The antibody of claim 1, wherein the antibody has an IC50 of: at least 1.4 ng/ml for 1-benzylpiperazine (BZP), 0.813 ng/ml for 4-OH benzylpiperazine (4-OH-BZP; p-OH-BZP), 1.137 ng/ml for 3-(Piperazin-1ylmethyl)phenol, 1.379 ng/ml for 1-Piperonylpiperazine, and about 2.646 ng/ml for N-(3-Methylbenzyl)piperazine.

* * * * *